Figure 1:

United States Patent [19]

Nurmi et al.

[11] Patent Number: 4,689,226

[45] Date of Patent: Aug. 25, 1987

[54] PROCESS FOR THE PRODUCTION OF A BACTERIAL PREPARATION FOR THE PROPHYLAXIS OF INTESTINAL DISTURBANCES IN POULTRY

[75] Inventors: Esko V. Nurmi; Jarita E. Schneitz; Pirjo H. Mäkela, all of Helsinki, Finland

[73] Assignee: Farmos-Yhtyma Oy, Turku, Finland

[21] Appl. No.: 511,019

[22] Filed: Jul. 5, 1983

Related U.S. Application Data

[63] Continuation of Ser. No. 223,796, Jan. 9, 1981, abandoned.

[30] Foreign Application Priority Data

Jan. 11, 1980 [FI] Finland .................................. 800077

[51] Int. Cl.$^4$ ............................................. A01N 63/00
[52] U.S. Cl. ..................................... 424/93; 435/253; 435/801; 426/2
[58] Field of Search ...................... 435/253, 42, 801; 426/2, 61, 635, 630, 623, 807; 424/93

[56] References Cited

U.S. PATENT DOCUMENTS 2,119,739  6/1938  Farr ..................................... 435/253
2,744,015  5/1956  Katsube ................................ 424/93

FOREIGN PATENT DOCUMENTS 0006695  4/1979  European Pat. Off. .
1254821  11/1967  Fed. Rep. of Germany .
1015956  7/1963  United Kingdom .
1167196  10/1969  United Kingdom .
1208599  10/1970  United Kingdom .

OTHER PUBLICATIONS

Marjatta Rantala, "Cultivation of a Bacterial Flora Able to Prevent the Colonization of *Salmonella infantis* in the Intestines of Broiler Chickens, and its Use", 1974, pp. 75-80 with Biological Abstract.

G. H. Snoeyenbos et al, "Protecting Chicks and Poults from Salmonellae by Oral Administration of "Normal gut Microflora", Apr.-Jun. 1978, pp. 273-287 with Biological Abstract.

G. H. Snoeyenbos et al, "Further Studies on Competitive Exclusion for controlling Salomnella in Chickens", 1979, pp. 904-914.

M. Rantala and E. Nurmi, "Prevention of the Growth of *Salmonella infantis* in Chicks by the Flora of the Alimentary Tract of Chickens", 2/26/73, pp. 75-80.

Primary Examiner—R. B. Penland
Attorney, Agent, or Firm—Armstrong, Nikaido, Marmelstein & Kubovcik

[57] ABSTRACT

The invention provides a bacterial preparation for the prophylaxis of intestinal disturbances, especially salmonella infections, in poultry, made by anaerobically cultivating either separately or together bacterial strains of normal alimentary tract bacterial species, optionally in the presence of epithelial cells from the alimentary tract, for example the crop of a poult, and isolating the cultivated bacteria from the nutrient medium and making a preparation of them, for instance by lyophilization. The only bacterial strains used are those having an adhesion efficiency onto the epithelial cells of the alimentary tract of the poult of at least 10 bacteria per epithelial cell.

7 Claims, 2 Drawing Figures

PROCESS FOR THE PRODUCTION OF A BACTERIAL PREPARATION FOR THE PROPHYLAXIS OF INTESTINAL DISTURBANCES IN POULTRY

This is a continuation of application Ser. No. 223,796, filed Jan. 9, 1981 and now abandoned.

DESCRIPTION

This invention relates to the production of a bacterial preparation for the prevention of intestinal disturbances, particularly salmonella infections, in poultry.

Poultry is the most important source of human salmonella infections. In Canada it has been calculated that 77 percent of human salmonella infections originates from poultry (B. J. Finn and B. Mehr, Proceedings of the International Symposium on Salmonella and Prospects for Control; Ontario, Canada 1977). In Finland the same has been apparently observed in the 1970's. In 1971 a large salmonella epidemic in broilers spread in Finland, *S. infantis* being the most common salmonella type. The epidemic caused very large economical losses to the breeders and the slaughter-houses. More than 10,000 fowls had to be destroyed as unfit for human food and hundreds of thousands of fowls had to be heated before marketing, which reduced their sales value. Correspondingly, since the year 1971 the human salmonella cases caused by *S. infantis* have been the second most common. In 1972 about five hundred humans were found to be taken ill with intestinal infection caused by *S. infantis*. The contaminated broilers thus caused a serious national health and economy problem.

In Sweden, where as well as in Finland the national government undertakes legal procedures to combat salmonella infections in the poultry, more than ten million Swedish crowns yearly are paid as compensation to the breeders for the destroyed chickens. In Canada the very big national health risk caused by salmonella infections of the poultry has recently been acknowledged. The losses caused both by human and animal infections have been estimated as approximately 30 million dollars yearly. In the U.S.A. such losses are estimated to be over 300 million dollars yearly.

Traditional methods used to prevent these salmonella infections are supervising the animals' feed by bacteriological sampling, watching the sanitation of the farms and slaughtering, and bacteriological investigation of foodstuffs for sale. With these methods the salmonella situation of most domestic animals can be reasonably well kept under control.

Poultry and especially the mass-breeding product, the broiler, are an exception in this respect. In a study, carried out at the State Veterinary Medical Institute in Finland, it was confirmed that a probable reason for the great susceptibility of broilers to salmonella colonization (growth and attachment) in the intestines was the delayed development of the normal intestinal flora. This delay results from the modern mass-breeding methods of animals (E. Nurmi and M. Rantala, Nature 241, 210–211, 1973).

Following this study novel possibilities of preventing salmonella infections in yound chickens have been explored. It was found that a culture of bacterial cells enriched from the intestines of a grown hen, when given to chickens aged 1-2 days, prevented the attachment and growth of salmonella in the intestines. This method has been very effective in small scale laboratory tests and also promising in large field trails. A drawback and hindrance of the wide use of this method in different countries has been the fact that the composition of the product cannot be standardized so that the product could be stored without changes in composition and effect. Because the starting material is always the intestinal content of an adult fowl, the preparation may contain pathogenic viruses, bacteria or parasites, which may be injurious and dangerous to the health of the chicks.

Antibiotics and chemotherapeutics have also been used in preventing or eliminating salmonella infections. However, it has been necessary to give up this method, because treatment with these substances cannot be continued throughout the breeding period till slaughtering without leaving residues in the meat and eggs. Foodstuffs for human use are not allowed to contain traces of such substances. On the other hand, interrupted treatment with antibiotics and chemotherapeutics is detrimental, because these substances destroy the normal intestinal flora. As a result, the animals are more sensitive to infections after the treatment has been finished. Attempts have been made to produce bacterial preparations, useful for the prophylaxis of salmonella and other intestinal infections in animals.

Swedish Patent Publication No. 371 209 describes a method for the preparation of a bacterial composition containing *Streptococcus faecium,* useful for the prophylaxis of intestinal infections in swine and calves.

British Pat. No. 1,208,599 describes a method for the selective cultivation of lactobacteria, wherein the bacteria, which may be of intestinal origin as one feature of the invention, are cultured on a nutrient medium containing intestinal mucosa.

British Pat. No. 1,167,196 describes the manufacture of a Lactobacillus bacterial preparation, useful for the inhibition of intestinal infections, wherein the starting material may be of intestinal origin. Pathogenic bacteria are removed by keeping the intestinal bacteria mixture in an acidic solution, wherein the pathogenic bacteria die. The surviving Lactobacillus bacteria are isolated, cultured and fed to mammals, after which the steps of isolating and culturing the bacteria are repeated. In this way, the activity of the finally isolated lactic acid bacteria has been enhanced.

The U.S. Pat. No. 3,953,609 describes a method of feeding mammals a strain of *Lactobacillus lactis* in order to inhibit intestinal infections.

These patents do not, however, disclose any useful preparation for the prophylaxis of intestinal infections in poultry. The preparations described have not achieved any wider use, because they have proved to be ineffective against infections in poultry.

Somewhat better results have been achieved with the preparations in swine and calves. The greatest disadvantage of the marketed preparations is that the bacteria of the composition have not preserved their ability to adhere to the intestinal mucosa.

The present invention provides a bacterial preparation able to effectively prevent salmonella infections and other intestinal diseases in poultry in an economically advantageous manner.

Supervising the animal fodder and hygienic conditions by bacterial sampling as described above, obligatory heating of fodder and foodstuff and destroying of infected goods are quite effective methods in the prophylaxis of salmonella infections in man. These methods are, however, so expensive, that it is almost impossible to apply them effectively in any country. In Canada the estimated costs of effectively supervising and preventing salmonella infections were 300 million dollars in 1977. The benefit obtained was estimated at 23 million dollars.

The method of the present invention is economically very advantageous. Tests have proved that salmonella infections can be effectively inhibited in poultry by this method. It does not suffer from the disadvantages and dangers to health, which the previous experimentally used (and, with respect to its composition, undefined) bacterial preparation suffered from. It is made up of pure cultures and can be easily standardized.

It has been found, that in order to get an effective preparation, it is essential to cultivate selected bacterial strains, which have a good ability to adhere to the epithelial cells of the alimentary tract. This results in a preparation consisting mainly of bacteria with a good ability to adhere in the epithelial cells of the alimentary tract. The ability to adhere is essential, otherwise the preparation does not work.

The present invention provides a process for the manufacture of a bacterial preparation for the prophylaxis of intestinal disturbances in poultry, which comprises anaerobically cultivating separately or together bacterial strains of normal alimentary tract bacterial species having an adhesion efficiency onto the epithelial cells of the alimentary tract of poultry of at least 10 bacteria per epithelial cell, and isolating the cultivated bacteria.

The bacterial strains to be cultivated are selected from bacterial species normally occurring in the alimentary tract in poultry. The bacterial strains are anaerobically incubated separately or together by well-known methods, preferably together with epithelial cells from the alimentary tract, for example from the crop of a chicken. After the cultivation, the bacteria are isolated from the culture broth and finished to a preparation, for instance by lyophilization.

It is essential that only bacterial strains with a verified good ability to adhere to the epithelial cells of the alimentary tract of the species, in which it is to be used, are chosen for the cultivation. The test for adhesion is carried out by some known method, for instance according to the Fuller adhesion test (Fuller, R., J. Appl. Bact. 36, 1973, 131–139). When the Fuller test is used, the only bacterial strains selected for cultivation are those having an adhesion efficiency of at least 10 bacteria per epithelial cell.

Especially good results are obtained when two or more bacterial strains are cultivated together.

The isolation of suitable bacteria strains can be performed as follows:

The content of the alimentary tract of an adult chicken is mechanically removed. After this, loose and weakly attached bacteria are removed, for instance by washing with a phosphate buffered saline.

The washed alimentary tract, or part of it, preferably the crop or the caecum with the attached bacteria remaining, is minced, suitably diluted and cultured to obtain pure cultures. After this, their adhering ability to the epithelial cells is controlled by some known test method. Bacterial strains with a good adhering ability are selected for the cultivation of the final preparation.

In order to enhance and preserve a good adhering ability of the bacterial strains, they can be fed to poults and isolated again from the alimentary tract by repeating the steps mentioned above.

The good adhering ability can also be preserved by incubating the bacterial strains together with sterile epithelial cells from the alimentary tract, preferably the crops of poults.

The process for preparation of the product and the use of the said product for the prophylaxis of salmonella infections in broilers are described in the following Example and experiments. Although the experiments describe the observed effects in broiler chickens only, the invention is obviously not limited to these birds. The invention can be generally applied in the poultry industry.

EXAMPLE 1

Manufacturing of the bacterial preparation

Isolation of the bacteria

The crop and/or the caecum of an adult chicken is removed, aseptically opened and mechanically cleaned. After this the crop and/or the caecum is washed four times with 100 ml of sterile phosphate buffered saline, which has the following composition (Fuller R, Turvey A, 1971: Bacteria associated with the intestinal wall of the fowl (*Gallus domesticus*). J. Appl. Bact. 34, s. 617–622):

NaCl: 8.0 g
$K_2HPO_4$: 1.21 g
$KH_2PO_4$: 0.34 g
distilled water: 1000 ml.

The washing removes loose and weakly attached bacteria. After this the crop and/or the caecum with their attached bacteria are minced and suspended into a salt solution of the composition mentioned above using conventional microbiological homogenizing processes. Of the homogenate serial 10-fold dilutions are made into a dilution solution, by a modification of the dilution solution, described in Holdeman, L. W. and W. E. C. Moore (ed.) 1977, Anaerobic Laboratory Manual 4 ed., Virginia Polytechnical Institute and State University Anaerobic Laboratory, Blacksburg. The dilution solution used has the following composition:

gelatine: 2.0 g
$K_2HPO_4$: 4.105 g
$KH_2PO_4$: 1.636 g
distilled water: 1000 ml.

After this, plating on Lactobacillus selective medium is performed (Sutter, W. L. and W. L. Vargo and S. N. Finegold (ed.) Wadsworth Anaerobic Bacteriology Manual, 1975, Los Angeles, 2 edition). The composition of the nutrient medium is LBS-agar (BBL): 8.40 g
tomato juice: 40.00 ml
distilled water: 60.00 ml
glacial acetic acid: 0.13 ml.

The plate incubation is carried out anaerobically for 5 days at $+35°$ C. At the end of the incubation, bacteria strains, likely to have a good ability to attach to the epithelial cells of a chicken, are isolated. The selection is performed by the eye, depending on the shape of the colonies. The adhering ability is then determined for instance by Fuller's test (Fuller, R., J. Appl. Bact. 36, 1973, 131–139). The isolated strains are cultured for example in a MRS-medium, divided into small aliquots, and deep-frozen ($-70°$ C.) or lyophilized. The composition of the MRS-medium is as follows (de Man, Rogosa, Sharpe; OXOID Ltd, Hampshire, code CM 359):

bacteriological peptone (oxoid L34): 10.0 g/l

'lab lemco' meal (oxoid L29): 8.0 g/l
yeast extract (oxoid L21): 4.0 g/l
dextrose: 20.0 g/l
tween 20: 1.0 mg/l
$K_2HPO_4$: 2.0 g/l
sodium acetate $\times 3H_2O$: 5.0 g/l
triammonium citrate: 2.0 g/l
$MgSO_4 \times 7H_2O$: 0.2 g/l
$MnSO_4 \times 4H_2O$, pH 6,2: 0.05 g/l.

The Fuller test is performed as follows:

(a) Preparation of the epithelial cell suspension

In the test epithelial cells from the crop of chicks aged 1-2 weeks are used. The chicks are fasted for two days before they are killed, in order to partly remove bacteria from the crop. The crop is removed and opened as aseptically as possible. After this it is washed twice with 100 ml of a buffered salt solution. The epithelial cells of the washed crop are scraped off with a sterile microscope slide and the scrapings are suspended into 10 ml of a buffered salt solution. The cell concentration of the suspension is adjusted to $3.5 \times 10^5/0.4$ ml.

(b) Preparation of the bacterial suspension

The pure cultures are grown anaerobically for 2 days at $+35°$ C. 10 ml of the cultivated bacterial suspension is centrifuged (10 min/2600 revolutions). After centrifuging the solution is removed and the bacteria are suspended into 10 ml of a buffered salt solution. The cell concentration of the bacterial suspension is adjusted to approximately $1.5 \times 10^7/0.1$ ml.

(c) The test for adhesion to epithelial cells of the crop

To 0.4 ml of the epithelial cell suspension are added 0.1 ml of the bacterial suspension. The combined suspension containing epithelial cells and bacteria is incubated for 30 minutes at $+35°$ C. in a cell mixer, the rotative speed of which is 20 revolutions/minute. In the tests a HETO-mixer was used (FASEMOTORTYPE RD 12×R; BIRKEFOD, DENMARK).

After the incubation, a normal Gram-stain preparation is made in order to determine the adhesion. In the Gram-stain the epithelial cells are negatively stained, in other words, they become red, while the bacterial cells are positively stained, they become dark blue. The adhesion can also be determined directly without staining by phase contrast microscopy.

Figure 2:
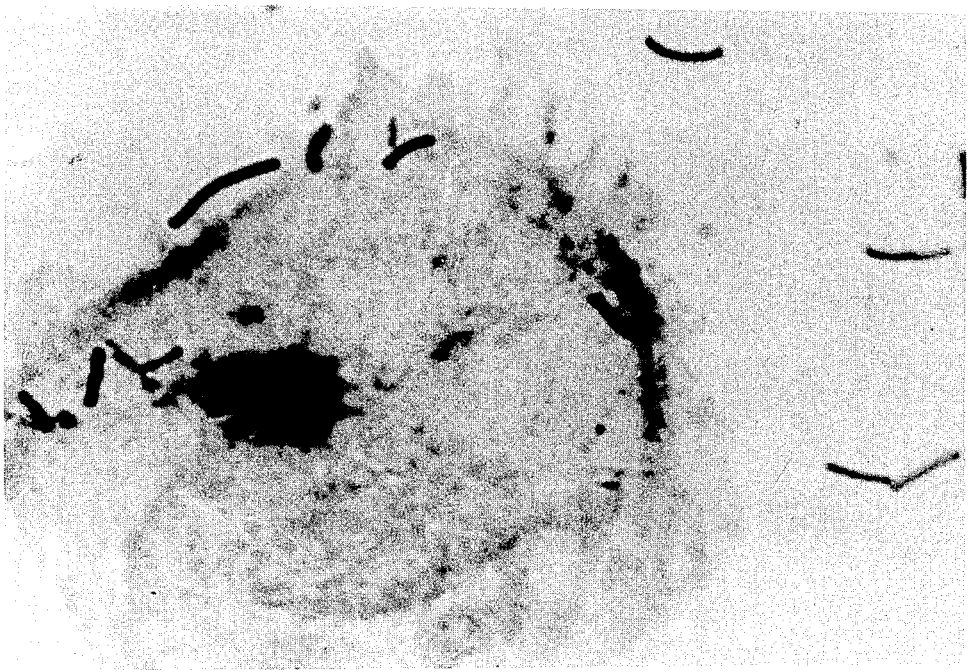

The selected strains typically belong to *Lactobacillus acidophilus, L. fermentum, L. lactis* and different *Clostridium* species. The strains can be identified by the API-50 Lactobacillus test (API system, La Balme-Les Grottes, France). The identification is of course not necessary to carry out. FIGS. 1 and 2 are microscopy pictures showing the epithelial cell with its attached bacteria. These pictures demonstrate very clearly the difference between the well adhering and weakly adhering bacteria. FIG. 1 demonstrates a well adhering bacteria strain and FIG. 2 demonstrates a weakly adhering strain.

Preparation of the final culture

The deep-frozen strains are thawed and a rich inoculum thereof is transferred into 10 ml of a MRS-broth or a VL-broth (Barnes, E. M., and Impey, C. S., Br. Poult. Sci. 11, 1970, 467-481).

The VL-broth has the following composition:
Trypticase peptone (BBL 11921): 10.0 g/l
Yeast extract (oxoid L21): 5.0 g/l
Meat extract (oxoid 'lab lemco' L30): 3.0 g/l
Agar: 0.6 g/l
NaCl: 5.0 g/l
Cysteine hydrochloride: 0.4 g/l
Glucose, pH 7.2-7.4: 2.5 g/l.

At this activating stage the strain are incubated separately overnight anaerobically at $+35°$ C. After the incubation a mixed culture is made by inoculating a few drops of each pure culture into the broth. After the incubation, which is carried out anaerobically for two days, the bacterial cells are isolated from the culture broth and finished to the final preparation, for example by lyophilization.

The bacterial preparation can also be made out of non-activated, newly thawed strains. In that case the deep-frozen strains are thawed, after which the mixture suspension is made directly and incubated as above.

Therapeutic experiments

Chick experiment No. 1

The preparation was made, according to the method above, by incubating 8 different Lactobacillus strains isolated from the crops of 4 chicks and from the caeca of 4 chicks. One of the strains was *Lactobacillus fermentum*, one *L. lactis* and six *L. acidophilus*. The adhesion efficiency of all the strains was above 10 bacteria per epithelial cell. The pure cultures were first incubated in MRS-broth separately at $+35°$ C. for one day before preparing the mixed culture as described before. 1 ml of the bacterial suspension was administered into the crop of the chicks. The chicks were one day old.

After 24 hours the chicks were infected with *Salmonella infantis* by administering approximately 1000 viable cells from a twenty-four hour broth culture into the crop.

After one week the chicks were asphyxiated by $CO_2$, the contents and walls of the caecum and part of the small intestine were incubated in salmonella-enrichment medium overnight at $+35°$ C., three loopfuls of the culture were streaked on a medium selective for enterobacteria. After twenty-four hours incubation, salmonella colonies were identified using conventional methods.

There were two groups of chicks: the treatment group (treated with the mixed culture) and the salmonella control group (untreated), both of them containing 6 chicks. Result: In the treatment group none of the chicks had been infected, while salmonellas were recovered from all the chicks in the control group.

Chick experiment No. 2

The preparation and the experiment were carried out according to the previous experiment, except that the 6 best adhering strains were selected from the 8 strains used in experiment No. 1, 4 strains isolated from the crop and 2 strains from the caecum. These 6 Lactobacillus strains were used in this experiment. The minimum adhesion efficiency was 20-30 bacteria per epithelial cell.

Result: In the treatment group none of the chicks had been infected, while salmonellas were recovered from five of six chicks in the control group.

Chick experiment No. 3

The preparation and the experiment were carried out according to experiments No. 1 and 2, except that the two most poorly adhering strains of the six strains used in experiment No. 2 were rejected. The four strains left, of which two were isolated from the crop and two from the caecum, were cultivated. The minimum adhesion efficiency was 40-50 bacteria per epithelial cell.

Result: In the treatment group none of the chicks had been infected, while salmonellas were recovered from all the chicks in the control group.

Chick experiment No. 4

The preparation and the experiment were carried out according to experiment No. 3, except that the pure cultures were not activated. Separate cultivation of the pure cultures for 2 days at +35° C. and combining just before feeding to the chicks were also tested. Furthermore, the stimulating effect of a pasteurized minced crop on the protective capacity of the preparation was investigated. The minced crop was obtained from 6 days old chicks, which were fasted for two days before they were killed. Before mincing, the crops were washed five times with 100 ml of a buffered sodium chloride solution.

Groups:

Group I: The pure cultures were grown separately 2 days at +35° C. together with a pasteurized minced crop.

Group II: The pure cultures were grown together 2 days at +35° C. together with a pasteurized minced crop.

Group III: The pure cultures were grown separately 2 days at 35° C. and combined just before they were fed to the chicks. The cultivation was performed without any minced crop.

Group IV: The same as Group III, except that all the strains were grown together from the very beginning.

Group V: Salmonella control group.

Results:

| CHICKS | GROUPS | | | | |
|---|---|---|---|---|---|
| | I | II | III | IV | V |
| 1 | + | − | + | − | + |
| 2 | + | − | + | − | − |
| 3 | + | − | + | − | + |
| 4 | + | − | + | − | + |
| 5 | + | − | + | − | + |
| 6 | + | − | + | − | + |

In the table above + means that the chick had become infected with salmonella infection, while − means that no salmonella could be isolated from the chick.

Inhibiting effect is observed in those groups (II and IV), in which the adhering bacterial strains were grown together.

Chick experiment No. 5

The preparation was made by growing separately 4 Clostridium strains and 10 Lactobacillus strains, isolated from the caecum of an adult chicken for 2 days at +35° C. in their own nutrient media. The strains were combined just before they were administered to the chicks. The experiment was performed as before.

Result: In the treatment group salmonella were recovered from two of six chicks, while all the chicks in the control group had become infected with salmonella.

In addition to the inhibition of salmonella, an improvement of the health and a faster growth were observed in the chicks treated with the bacterial preparation.

We claim:

1. A method for the prophylaxis of intestinal disturbances in poultry caused by infections of pathogenic bacteria which comprises feeding to said poultry an effective amount of a bacterial preparation consisting essentially of at least four anaerobically co-cultured strains of normal alimentary tract bacterial species, said strains being chosen from those normally present in the alimentary tract of poultry, and each said strain being selected for having an adhesion efficiency onto the epithelial cells of the alimentary tract of poultry as determined by the Fuller adhesion test, of at least 10 bacteria per epithelial cell.

2. A bacterial preparation for the prophylaxis of intestinal disturbances in poultry caused by infections of pathogenic bacteria and consisting essentially of at least four anaerobically co-cultured strains of normal alimentary tract bacterial species, said strains being chosen from those normally present in the alimentary tract of poultry and each of said strains being selected for having an adhesion efficiency onto the epithelial cells of the alimentary tract of poultry, as determined by the Fuller adhesion test, of at least 10 bacteria per epithelial cell.

3. A bacterial preparation according to claim 2 in which the bacteria are co-cultured in the presence of epithelial cells from the alimentary tract of poultry.

4. A bacterial preparation according to claim 2 wherein 4–8 different bacterial strains are co-cultured.

5. A bacterial preparation according to claim 2 wherein the selected bacterial strains are strains of Lactobacilli.

6. A bacterial preparation according to claim 2 wherein the selected bacterial strains are strains of Lactobacillus and Clostridium species.

7. A bacterial preparation according to claim 2 wherein the bacterial strains are strains of one or more of *Lactobacillus fermentum, L. lactis, L. acidophilus,* or *Clostridium.*

* * * * *